United States Patent
Takeuchi et al.

(10) Patent No.: US 6,943,004 B1
(45) Date of Patent: Sep. 13, 2005

(54) TRANSFORMED MICROORGANISM AND PROCESS FOR PRODUCING D-AMINOACYLASE

(75) Inventors: Ken-ichi Takeuchi, Gifu (JP); Yoshinao Koide, Gifu (JP); Yoshihiko Hirose, Gifu (JP); Mitsuaki Moriguchi, Oita (JP); Kimiyasu Isobe, Iwate (JP)

(73) Assignee: Amano Enzyme Inc., Nagoya (JP)

( * ) Notice: Subject to any disclaimer, the term of this patent is extended or adjusted under 35 U.S.C. 154(b) by 266 days.

(21) Appl. No.: 10/009,782

(22) PCT Filed: Jun. 15, 2000

(86) PCT No.: PCT/JP00/03932
§ 371 (c)(1),
(2), (4) Date: Mar. 25, 2002

(87) PCT Pub. No.: WO00/78926
PCT Pub. Date: Dec. 28, 2000

(30) Foreign Application Priority Data

Jun. 17, 1999 (JP) ............................................. 11/170555

(51) Int. Cl.[7] ............................ C12N 9/78; C12N 1/20; C12N 15/00; C12P 21/06; C07H 21/02

(52) U.S. Cl. ............... 435/227; 435/252.33; 435/320.1; 435/69.1; 435/252.3; 536/23.1; 536/23.2

(58) Field of Search .............................. 435/227, 320.1, 435/69.1, 252.33; 536/23.1

(56) References Cited

U.S. PATENT DOCUMENTS 5,916,774 A * 6/1999 Tokujama et al. .......... 435/71.2
6,030,823 A * 2/2000 Tokujama et al. .......... 435/227
6,514,742 B1 * 2/2003 Mitsuhashi et al. ........ 435/277

FOREIGN PATENT DOCUMENTS

JP 62-163689 7/1987
WO 90/02177 3/1990

OTHER PUBLICATIONS

M. Wakayama et al.: "Purification and characterization of L–aminoacylase from *Pseudomonas maltophila* B1" Journal of Fermentation and Boengineering, vol. 85, No. 3, pp. 278–282 1998.
M. Wakayama et al.: "Cloning and sequencing of a gene encoding D–aminoacylase from *Alcaligenes xylosoxydans* subsp. *xylosoxydans* A–6 and expression of the gene in *Escherichia coli*" Bioscience, Biotechnology and Biochemistry, vol. 59, No. 11, pp. 2115–2119 1995.
M. Wakayama et al.: "Overproduction of D–aminoacylase from *Alcaligenes xylosoxydans* subsp. *xylosoxydans* A–6 in *Escherichia coli* and its purification" Protein Expression and Purification, vol. 7, No. 4, pp. 395–399 1996.
J–M. Farah et al.: "Mechanistic analysis of the argE–encoded N–acetylornithine deacetylase" Biochemistry, vol. 39, No. 6, pp. 1285–1293 Dec. 2000.
M. Wakayama et al.:"Role of conserved histidine residues in D–aminoacylase from *Alcaligenes xylosoxydans* subsp. *xylosoxydans* A–6" Bioscience, Biotechnology, and Biochemistry, vol. 64, No. 1, pp. 1–8 Jan. 2000.

* cited by examiner

Primary Examiner—Rebecca E. Prouty
Assistant Examiner—M. Walicka
(74) Attorney, Agent, or Firm—Oblon, Spivak, McClelland, Maier & Neustadt, P.C.

(57) ABSTRACT

A transformed microorganism prepared by inserting into a host microorganism with zinc tolerance a D-aminoacylase-producing gene which selectively produces D-aminoacylase alone between D-aminoacylase and L-aminoacylase. A process comprising culturing the transformed microorganism in a culture medium containing zinc ion and obtaining D-aminoacylase from the culture at a high efficiency.

20 Claims, 2 Drawing Sheets

TRANSFORMED MICROORGANISM AND PROCESS FOR PRODUCING D-AMINOACYLASE

CROSS-REFERENCE TO RELATED APPLICATIONS

This application is a national-stage filing under 35 U.S.C. §371 of PCT/JP00/03932, filed Jun. 15, 2000. This application claims priority under 35 U.S.C. §119 to JAPAN 11/170555, filed Jun. 17, 1999.

REFERENCE TO SEQUENCE LISTING

This application contains a sequence listing of nucleic acid and amino acid sequences.

BACKGROUND OF THE INVENTION

1. Field of the Invention

The present invention relates to a transformed microorganism prepared by inserting into a zinc-tolerant microorganism a D-aminoacylase-producing gene which selectively produces D-aminoacylase alone between D-aminoacylase and L-aminoacylase, and a process for producing D-aminoacylase by utilizing the transformed microorganism.

2. Description of the Related Art

D-aminoacylase is an industrially useful enzyme for the production of D-amino acids of high optical purity, which are used for the side chains of antibiotics, peptide drugs and the like.

Chemical and Pharmaceutical Bulletin 26, 2698 (1978) discloses *Pseudomonas* sp. AAA6029 strain as a microorganism simultaneously producing both D-aminoacylase and L-aminoacylase.

Japanese Patent Application Laid-open No. Sho-53-59092 discloses actinomycetes, such as *Streptomyces olibaceus* S•6245. The use of these microorganisms results in the simultaneous production of both optical isomers of aminoacylase, D-aminoacylase and L-aminoacylase. While these organisms are capable of producing D-aminoacylase, it is necessary to separate this enzyme from its optical isomer, L-aminoacylase. Thus, laborious and costly procedures are disadvantageously required for the separation of the two.

Japanese Patent Application Laid-open No. Hei-1-5488 discloses *Alcaligenes denitrificans* subsp. *xylosoxydans* M1-4 strain as a microorganism that selectively produces D-aminoacylase alone.

If this bacterial strain is utilized, no laborious work is required for the separation of D-aminoacylase from L-aminoacylase. However, the capacity of this bacterial strain to produce D-aminoacylase is insufficient. Furthermore, the nucleotide sequence of the D-aminoacylase-producing gene is not elucidated in Japanese Patent Application Laid-open No. Hei-1-5488. Thus, this document does not describe how to modify the D-aminoacylase gene so as to improve its D-aminoacylase-producing capacity or describe the creation of a transformed bacterium with an ability to produce higher amounts of D-aminoacylase.

BRIEF SUMMARY OF THE INVENTION

In view of the above, the present inventors Moriguchi, et al. elucidated the structure of the D-aminoacylase-producing gene in the *Alcaligenes xylosoxydans* subsp. *xylosoxydans* A-6 strain and demonstrated its nucleotide sequence, which appears as SEQ ID NO: 1 in the sequence listing. Further, it was found that genetic modification of the D-aminoacylase-producing gene successfully improved the D-aminoacylase-producing capacity of the resulting transformed bacterium (Protein Expression and Purification 7, 395–399 (1996)).

DETAILED DESCRIPTION OF THE INVENTION

Figure 1:
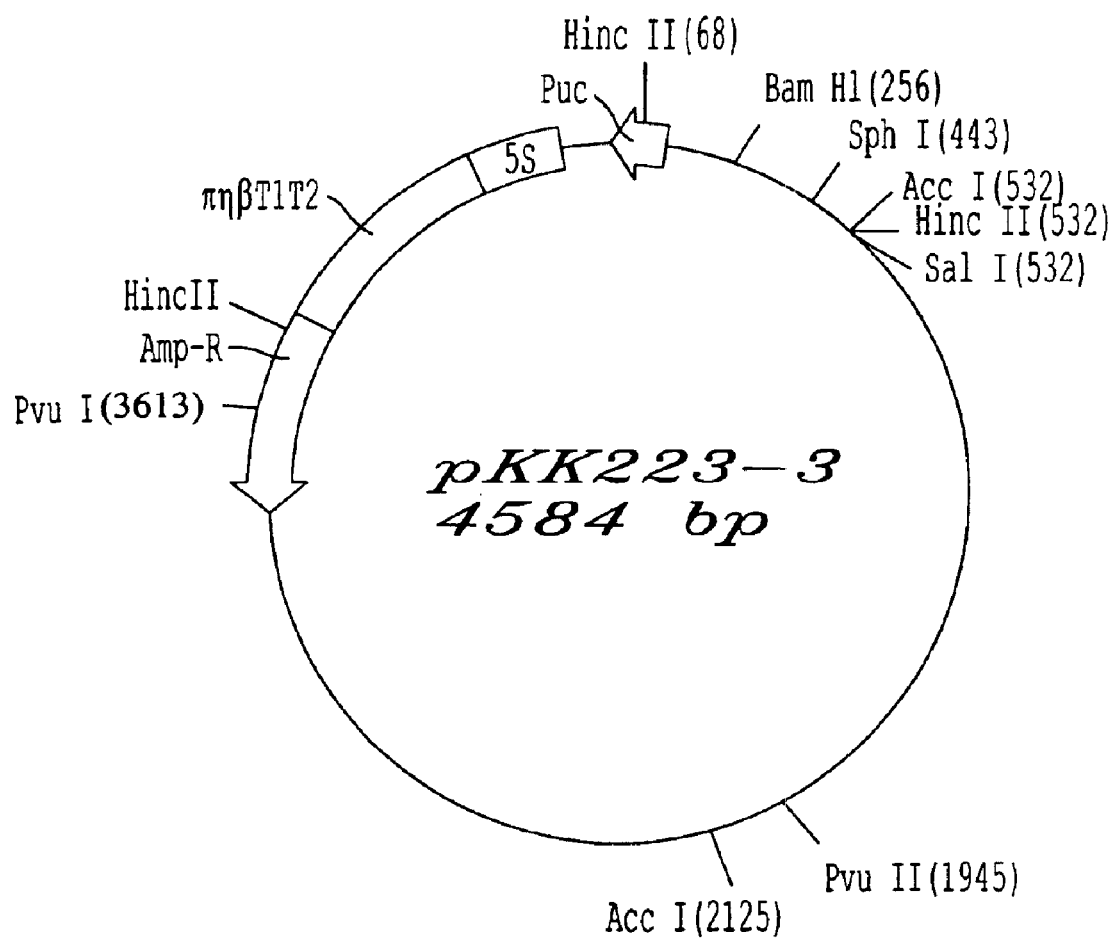
FIG. 1 schematically depicts the plasmid used for ligation with the D-aminoacylase-producing gene.

The inventors' subsequent research works have elucidated that the D-aminoacylase-producing capacities of various transformed bacteria with the aforementioned D-aminoacylase-producing gene inserted therein are greatly improved in zinc ion-containing culture media. It has also been found that the D-aminoacylase producing capacity of a transformed bacterium is prominently improved by controlling the zinc ion concentration within a predetermined range.

Furthermore, it has been found that the above-mentioned effect varies significantly depending on the type of a host microorganism and that a host microorganism with high such effect generally exerts zinc tolerance even prior to the transformation thereof. Herein, the term "zinc tolerance" means that the growth potency of a bacterium as measured on the basis of the cell weight (A660 nm) is hardly inhibited by the addition of zinc ion.

The findings mentioned above indicate the following two points: (1) The expression of a transformed microorganism with a D-aminoacylase-producing gene of SEQ ID NO: 1 is enhanced in the presence of a given quantity of zinc ion, though the reason has not been elucidated. (2) Since it is believed that zinc ion functions in an inhibiting manner on common microorganisms, a congenitally zinc tolerant microorganism should be selected as a host to insert the gene therein so as to sufficiently procure the effect of zinc ion.

Based on the above-mentioned points, the invention provides a microorganism transformed with a D-aminoacylase-producing gene, the D-aminoacylase-producing capacity of which can be greatly enhanced with the addition of zinc ion to a culture medium therefor. The invention further provides a process for producing D-aminoacylase using the transformed microorganism.

The transformed microorganism of the invention is a microorganism having acquired high-expression ability to produce D-aminoacylase in a zinc ion-containing culture medium. This transformed organism may be prepared by inserting a D-aminoacylase-producing gene into a zinc tolerant host microorganism wherein the expression of a gene product of the inserted gene is enhanced in the presence of zinc ion. The transformed microorganism is a microorganism transformed with a D-aminoacylase-producing gene, and due to the addition of zinc ion to the culture medium, the D-aminoacylase-producing potency thereof can be enhanced to maximum.

In the transformed microorganism of the invention, the D-aminoacylase-producing gene more preferably has a nucleotide sequence of SEQ ID NO: 1 or a nucleotide sequence hybridizing to the nucleotide sequence of SEQ ID NO: 1 under stringent conditions and effectively encoding D-aminoacylase. It has been confirmed that a D-aminoacylase-producing gene having a nucleotide sequence of SEQ ID NO: 1 is a gene the expression of a gene product of which can greatly be enhanced in the presence of zinc ion. Further, a gene of a nucleotide sequence hybridizing to the nucleotide sequence of SEQ ID NO: 1 under stringent conditions and effectively encoding D-aminoacylase can be expected to have similar characteristics.

More preferably, in the transformed microorganism of the invention, the host microorganism is *Escherichia coli*. It has been confirmed that *Escherichia coli* has zinc tolerance. Further, the mycological and physiological properties, culture conditions and maintenance conditions of *Escherichia coli* are well known. Thus, the production of D-aminoacylase at high efficiency can be done under readily controllable conditions.

Still more preferably, in the transformed microorganism of the invention, a D-aminoacylase-producing gene which is to be inserted into a host microorganism is subjected to at least one of the following modifications (1) and/or (2). (1) A modification for improving the translation efficiency, comprising designing a specific nucleotide sequence (GAAGGA) (SEQ ID NO: 3) in the ribosome-binding site and inserting the nucleotide sequence in the position of the ninth base upstream of the translation initiation point of the gene. This modification improves the translation efficiency of the D-aminoacylase-producing gene. (2) A modification for improving the gene expression efficiency, comprising creating a HindIII recognition site of *Escherichia coli* in the upstream and downstream of the gene, subsequently purifying and excising the resulting gene, and ligating the gene into an expression vector. This modification improves the expression efficiency of the D-aminoacylase-producing gene.

A zinc-tolerant microorganism is used as a host microorganism for obtaining a transformed microorganism in accordance with the invention. More specifically, a microorganism should be used, the growth potency of which in culture media, as measured on the basis of increase or decrease of the cell weight (A660 nm), is not significantly inhibited by the addition of zinc ion. Zinc tolerance may be evaluated by comparing the cell weight of microorganisms grown in a zinc-free culture medium with the cell weight of the same microorganism grown in a medium containing zinc. On the basis of the cell weight (A660 nm) of the microorganism in a zinc-free culture medium, the cell weight in the same culture medium under the same conditions except for the addition of 2 mM zinc either increases, or decreases within a range of 10%. Otherwise, the above-mentioned cell weight in the same culture medium under the same conditions except for the addition of 5 mM zinc increases, or decreases within a range of 20%.

Although the taxonomical group of the host microorganism is not limited, it is generally preferable to use such host microorganisms that have well known morphological and physiological properties and for which the culture conditions and maintenance conditions are also well known. A preferable example of such a host microorganism is *Escherichia coli*. Compared with *Escherichia coli*, microorganisms of the species *Alcaligenes xylosoxidans* including A-6 strain do not have zinc tolerance.

The means for inserting a D-aminoacylase-producing gene into a host microorganism is not specifically limited. For example, a D-aminoacylase-producing gene may be inserted into either a plasmid or a bacteriophage by ligation to plasmid or bacteriophage DNA.

The D-aminoacylase-producing gene in accordance with the invention is a gene selectively producing D-aminoacylase as opposed to producing both D-aminoacylase and L-aminoacylase. This gene is of a type in which the activity expression is enhanced in the presence of zinc ion in the culture medium. As a preferable example of such D-aminoacylase-producing gene, the gene with the nucleotide sequence of SEQ ID NO: 1 has been confirmed. Further, genes of nucleotide sequences hybridizing to the nucleotide sequence of SEQ ID NO: 1 under stringent conditions and effectively encoding D-aminoacylase are also preferable, except for genes which do not actually enhance the activity expression with zinc ion in the culture medium.

The D-aminoacylase-producing gene with the nucleotide sequence of SEQ ID NO: 1 was obtained from the *Alcaligenes xylosoxidans* subsp. *xylosoxidans* A-6 strain. The A-6 strain is a D-aminoacylase-producing strain obtained from soil in nature via screening.

The process for producing D-aminoacylase in accordance with the invention comprises culturing any transformed microorganism as described above in a culture medium containing zinc ion, and obtaining D-aminoacylase from the culture. Zinc ion can be provided by adding an appropriate amount of a zinc compound, such as zinc chloride and zinc sulfate, to the culture medium. This process enables the production of D-aminoacylase at a high efficiency.

In the process for producing D-aminoacylase in accordance with the invention, the concentration of zinc ion contained in the culture medium is preferably controlled to be in the range of 0.1 to 10 mM. This process enables to optimize the zinc ion concentration in the culture medium, and to produce D-aminoacylase at a particularly high efficiency.

In the process for producing D-aminoacylase, other procedures and conditions for carrying out the process are not specifically limited. Never the less, the culture is preferably carried out in a nutritious culture medium containing tac promoter-inducing substances (for example, isopropyl thiogalactoside (IPTG), lactose and the like) as inducers. Further, the concentration of lactose then is preferably adjusted to about 0.1 to 1%.

Best Mode for Carrying out the Invention

The best mode for carrying out the invention is described below in conjunction with a comparative example. The invention is not limited to the best mode for carrying out the invention.

Obtaining the D-Aminoacylase Gene and Determining its Nucleotide Sequence.

The chromosomal DNA obtained from *Alcaligenes xylosoxidans* subsp. *xylosxidans* A-6 strain was partially digested with restriction endonuclease Sau3AI, to obtain by fractionation DNA fragments of 2 to 9 Kb. The resulting DNA fragments were inserted in and ligated into the BamHI recognition site of a known plasmid, pUC118. *Escherichia coli* JM109was transformed with the ligated plasmid to obtain an ampicillin-resistant transformant strain. Among the thus obtained transformant strains, a strain with the ability to selectively produce D-aminoacylase alone was obtained. The transformant strain with this ability contained a plasmid with a 5.8-Kb insert fragment.

The 5.8-Kb insert fragment in the plasmid was trimmed down to deduce the position of the D-aminoacylase-producing gene. According to general methods, then, the nucleotide sequence as shown in SEQ ID NO:1 was determined for the DNA of about 2.0 Kb. An amino acid sequence corresponding to the nucleotide sequence is also shown in the sequence listing. Consequently, an open reading frame (ORF) consisting of 1452 nucleotides starting from ATG was confirmed.

Modification of the D-aminoacylase Gene

From the plasmid with the 5.8-Kb insert fragment was excised a 4-Kb DNA fragment via BamHI-HindIII digestion, which was then ligated into a known plasmid pUC118 to construct a ligated plasmid pAND118. Using the resulting plasmid, site-directed mutagenesis using primers was effected, to thereby prepare a ribosome-binding site (RBS)-modified plasmid pANSD1.

Using the plasmid pANSD1 as template, site-directed mutagenesis using primers was effected, thereby to prepare a plasmid pANSD1HE having an EcoRI recognition site and a HindIII recognition site immediately upstream the RBS and immediately downstream the ORF, respectively.

Figure 2:
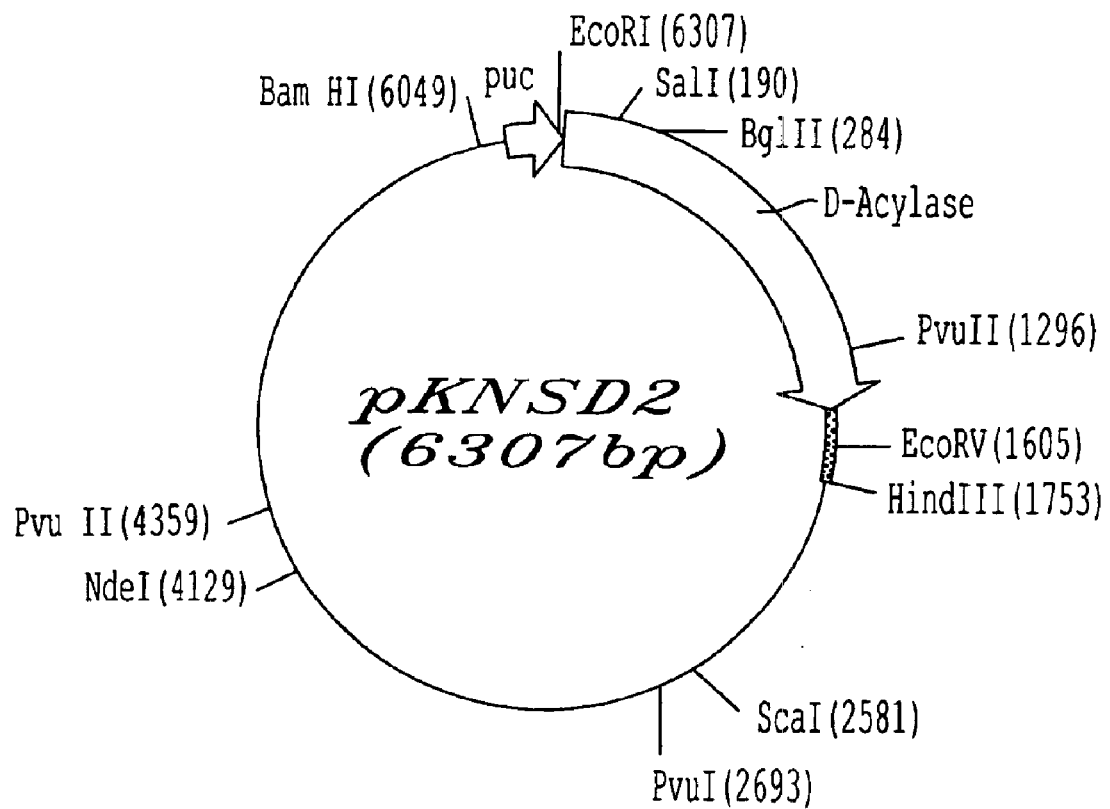
FIG. 2 schematically depicts the plasmid ligated with the D-aminoacylase-producing gene.
Figure 2:
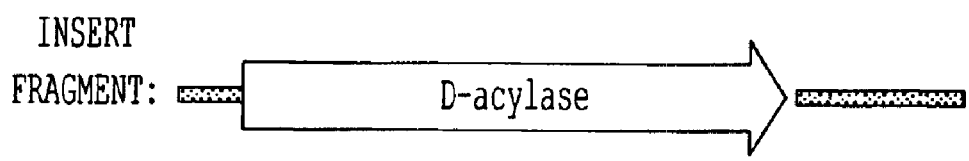

Then, the plasmid pANSD1HE was digested with restriction endonucleases EcoRI and HindIII to prepare a 1.8-Kb DNA fragment, which was inserted in and ligated at the EcoRI-HindIII site in the plasmid pKK223-3 shown in FIG. 1 to obtain the plasmid pKNSD2 shown in FIG. 2.

Transformation of Escherichia coli with the D-Aminoacylase Gene

The plasmid DNA was inserted into a host strain derived from the Escherichia coli K-12 strain by the D. HANAHAN's method (DNA Cloning, Vol. 1, 109–136, 1985), thereby to obtain a transformed Escherichia coli (E. coli) TG1/pKNSD2.

Zinc-Tolerance of the Bacterial Strain from which D-Aminoacylase Gene was Obtained The Alcaligenes xylosoxidans subsp. xylosoxidans A-6 strain was cultured at 30° C. for 24 hours in a culture medium (pH 7.2, zinc-free) containing 0.2% potassium dihydrogen phosphate, 0.2% dipotassium hydrogen phosphate, 2% polypeptone, 0.01% magnesium sulfate and 1% glycerin, and in culture media of the same composition but with addition of zinc oxide to concentrations 0.2 mM, 2.0 mM and 5.0 mM, respectively. After culturing, the cell weight (A660 nm) was measured to evaluate the zinc tolerance. Then, the pH of the culture media after culturing was measured. The results are shown in the column of "A-6 bacteria" in Table 1.

TABLE 1

| Microbial strain | Zinc concentration (mM) | Post-culture pH | Cell weight (A660) | Relative value (%) |
|---|---|---|---|---|
| A-6 bacteria | 0.0 | 7.58 | 8.09 | 100.0 |
|  | 0.2 | 7.62 | 7.75 | 95.8 |
|  | 2.0 | 7.56 | 5.23 | 64.6 |
|  | 5.0 | 7.68 | 3.34 | 41.3 |
| TG1 (host bacterium) | 0.0 | 5.01 | 5.68 | 100.0 |
|  | 0.2 | 4.99 | 5.93 | 104.4 |
|  | 2.0 | 4.98 | 5.55 | 97.7 |
|  | 5.0 | 5.01 | 4.98 | 87.7 |
| pKNSD2/TG1 (recombinant bacterium) | 0.0 | 5.00 | 6.45 | 100.0 |
|  | 0.2 | 5.01 | 6.70 | 103.9 |
|  | 2.0 | 4.98 | 6.09 | 94.4 |
|  | 5.0 | 5.01 | 5.47 | 84.8 |

Table 1 shows that the cell weight of the A-6 strain in the zinc-added culture media was greatly decreased (decreased by about 35% in the 2.0 mM zinc-added culture medium and by about 60% in the 5.0 mM zinc-added culture medium), compared with the cell weight of the A-6 strain in the zinc-free culture medium. This indicates that the A-6 strain was not zinc-tolerant.

Zinc Tolerance of Host Bacterium

The zinc tolerance of the strain derived from the Escherichia coli K-12 strain used as the host bacterium was examined, using a culture medium of the same composition as for the A-6 strain, by measuring the cell weight (A660 nm) in the same manner. The results are shown in the column of "TG1 (host bacterium)".

Table 1 shows that the cell weight of the host bacterium in the zinc-added culture media was not so greatly decreased (decreased by about 3% in the 2.0 mM zinc-added culture medium and by about 12% in the 5.0 mM zinc-added culture medium, and even increased in the 0.2mM zinc-added culture medium), compared with the cell weight of the host bacterium in the zinc-free culture medium. This indicates that the host bacterium was zinc-tolerant.

Zinc Tolerance of Transformed Escherichia coli

The zinc tolerance of the transformed Escherichia coli (E. coli) TG1/pKNSD2 was examined using a culture medium of the same composition as for the A-6 strain by measuring the cell weight (A660 nm) in the same manner. The results are shown in the column of "pKNSD2/TG1 (recombinant bacterium)".

Table 1 shows that the cell weight of the transformed bacterium in the zinc-added culture media was not so greatly decreased (decreased by about 5% in the 2.0 mM zinc-added culture medium and by about 15% in the 5.0 mM zinc-added culture medium, and even increased in the 0.2 mM zinc-added culture medium), compared with the cell weight of the transformed bacterium in the zinc-free culture medium. This indicates that the transformed Escherichia coli was zinc-tolerant.

(Effect of Zinc Addition on Transformed Escherichia coli)

The transformed Escherichia coli (E. coli) TG1/pKNSD2 was pre-cultured in a culture medium (pH 7.0) containing 1% bactotryptone, 0.5% bacto-yeast extract, 0.5% sodium chloride and 100 µg/ml ampicillin, at 30° C. for 16 hours.

Subsequently, the post-preculture transformed Escherichia coli was cultured at 30° C. for 24 hours in a culture medium (pH7.0, zinc-free) containing 0.2% potassium dihydrogen phosphate, 0.2% dipotassium hydrogen phosphate, 2% polypeptone, 0.01% magnesium sulfate, 1% glycerin and 0.1% lactose as an inducer, and culture media of the same composition but with addition of zinc oxide to concentrations 0.2 mM and 2.0 mM. Additionally, the broth-out pH of the culture broth as well as the enzyme activity (U/mL) of D-aminoacylase in the culture broth (A660 nm) was measured.

Consequently, the enzyme activity in the 0.2 mM zinc-added culture medium was 58.85 U/mL (broth-out pH of 5.03) and the enzyme activity in the 2.0 mM zinc-added culture medium was 109.79 U/mL (broth-out pH of 5.11), compared with the enzyme activity of 21.78 U/mL in the zinc-free culture medium (broth-out pH of 5.05). Thus, it has been confirmed that the addition of zinc ion, at least within a predetermined concentration range, greatly improves the D-aminoacylase-producing potency.

For comparison, additionally, the A-6 strain was pre-cultured in the culture medium for preculture (no ampicillin was however added) under the same conditions, and was then cultured in the culture medium of the same composition for culture, except for the change of the inducer from 0.1% of lactose to 0.1% of N-acetyl-D, L-leucine. Then, the broth-out pH of the culture broth as well as the enzyme activity (U/mL) of D-aminoacylase in the culture broth (A660 nm) was assayed.

Consequently, the enzyme activity in the 0.2 mm zinc-added culture medium was 0.12 U/ml (broth-out pH of 7.48) and the enzyme activity in the 2.0 mm zinc-added culture medium was 0.29 U/mL (broth-out pH of 7.43), compared with the enzyme activity of 029 U/ML in the zinc-free culture medium (broth-out pH of 7.47). Thus, no effect of zinc ion addition on the improvement of the D-aminoacylase-producing potency could be comfirmed.

INDUSTRIAL APPLICABILITY

As described above, D-aminoacylase, as an industrially useful enzyme, can be produced highly efficiently and selectively by using the transformed microorganism of the invention.

What is claimed is:

1. An isolated microorganism comprising a nucleic acid sequence that encodes the amino acid sequence of SEQ ID NO: 2, or a nucleic acid sequence from *Alcaligenes*, which encodes D-aminoacylase, which comprises the following sequence of restriction sites: Sal I, Bgl II and Pvu II, wherein said nucleic acid sequences comprise SEQ ID NO:3 in the ninth position upstream from the first nucleotide in the start codon; said microorganism is zinc resistant, and wherein the activity of D-amino acylase encoded by said nucleic acid sequence in said microorganism is enhanced in the presence of zinc ion.

2. The isolated microorganism of claim 1 that comprises a nucleic acid sequence that encodes the amino acid sequence of SEQ ID NO:2.

3. The isolated microorganism of claim 1 that comprises the nucleic acid sequence of SEQ ID NO: 1.

4. The isolated microorganism of claim 1 that comprises a nucleic acid from *Alcaligenes* which encodes D-aminoacylase, the activity of which is enhanced in the presence of zinc ion, wherein said nucleic acid comprises the following sequence of restriction sites Sal I, Bgl II and Pvu II, and comprises SEQ ID NO:3 in the ninth position upstream from the first nucleotide in the start codon.

5. The isolated microorganism of claim 1, wherein the aminoacylase encoding nucleic acid sequence is obtained from *Alcaligenes xylosoxidans*, subsp. *xylosoxidans* strain A-6.

6. The isolated microorganism of claim 1, wherein the aminoacylase encoding nucleic acid sequence is modified by:
   creating a Hind III recognition site upstream and downstream from the D-aminoacylase gene,
   excising or purifying the resulting modified gene and ligating the modified gene into an expression vector.

7. The isolated microorganism of claim 1, wherein the zinc resistance of the host microorganism is such that the cell weight of the microorganism either increases, or decreases, within a range of 10% in a culture medium with 2 mM zinc added thereto on the basis of the cell weight measured at A660 nm in a zinc-free culture medium.

8. The isolated microorganism of claim 1, wherein the zinc resistance of the microorganism is such that the cell weight of the microorganism either increases, or decreases, within a range of 20% in a culture medium with 5 mM zinc added thereto on the basis of the cell weight measured at A660 nm in a zinc-free culture medium.

9. The isolated microorganism of claim 1, which is *Escherichia coli*.

10. A process for producing D-aminoacylase comprising:
    culturing the isolated microorganism of claim 1 in a culture medium containing zinc and
    recovering D-aminoacylase.

11. The process of claim 10, further comprising culturing said microorganism in a medium containing a tac promoter-inducing substance.

12. The process of claim 10, wherein said promoter-inducing substance is isopropyl thiogalactoside (IPTG) or lactose.

13. The process of claim 10, wherein said culture medium has a concentration of lactose ranging from 0.1 to 1%.

14. An isolated nucleic acid sequence which encodes the amino acid sequence of SEQ ID NO: 2, or which encodes a D-aminoacylase from *Alcaligenes*, which comprises the following sequence of restriction sites: Sal I, Bgl II and Pvu II, wherein said isolated nucleic acid sequence comprises an upstream ribosome binding site comprising GAAGGA (SEQ ID NO: 3) in the ninth position upstream from the first nucleotide in the start codon.

15. The isolated nucleic acid sequence of claim 14, which encodes the amino acid sequence of SEQ ID NO:2.

16. The isolated nucleic acid sequence of claim 14, further comprising an EcoR I site before said Sal I site and a Hind III site after the Pvu II site.

17. A vector comprising the nucleic acid sequence of claim 14.

18. An isolated nucleic acid sequence from *Alcaligenes* that encodes a D-aminoacylase and which comprises the following sequence of restriction sites: Sal I, Bgl II and Pvu II, wherein said isolated nucleic acid sequence comprises an upstream ribosome binding site comprising GAAGGA (SEQ ID NO: 3) in the ninth position upstream from the first nucleotide in the start codon.

19. A vector comprising the nucleic acid sequence of claim 18.

20. A zinc-resistant host cell comprising the nucleic acid sequence of claim 18.

* * * * *

SEQUENCE LISTING

<160> NUMBER OF SEQ ID NOS: 3

<210> SEQ ID NO 1
<211> LENGTH: 1758
<212> TYPE: DNA
<213> ORGANISM: Alcaligenes xylosoxydans subsp. xylosoxydans
<220> FEATURE:
<221> NAME/KEY: CDS
<222> LOCATION: (34)..(1485)
<223> OTHER INFORMATION:

<400> SEQUENCE: 1

```
gaattccact tgatcgcgga aggagagatt tcc atg tcc caa tcc gat tcc cag         54
                                    Met Ser Gln Ser Asp Ser Gln
                                     1               5 ccc ttc gac ctg ctg ctc gcg ggc ggc acc ctc atc gac ggc agc aac        102
Pro Phe Asp Leu Leu Leu Ala Gly Gly Thr Leu Ile Asp Gly Ser Asn
         10                  15                  20 acc ccg ggg cgg cgc gcc gac ctg ggc gtg cgc ggc gac cgc atc gcc        150
Thr Pro Gly Arg Arg Ala Asp Leu Gly Val Arg Gly Asp Arg Ile Ala
     25                  30                  35 gcc atc ggc gat ctg tcg gac gcc gcc gcg cac acc cgg gtc gac gtg        198
Ala Ile Gly Asp Leu Ser Asp Ala Ala Ala His Thr Arg Val Asp Val
 40                  45                  50                  55 tcg ggc ctg gtg gtc gcg ccc ggc ttc atc gac tcg cac acc cac gac        246
Ser Gly Leu Val Val Ala Pro Gly Phe Ile Asp Ser His Thr His Asp
                 60                  65                  70 gac aac tac ctg ctc agg cgt cgc gac atg acg ccc aag atc tcg cag        294
Asp Asn Tyr Leu Leu Arg Arg Arg Asp Met Thr Pro Lys Ile Ser Gln
             75                  80                  85 ggc gtc acc acg gtg gtc acg ggc aat tgc ggc atc agc ctg gcg ccg        342
Gly Val Thr Thr Val Val Thr Gly Asn Cys Gly Ile Ser Leu Ala Pro
         90                  95                 100 ctg gcg cac gcc aac ccg ccc gcc ccc ctg gac ctg ctg gac gaa ggc        390
Leu Ala His Ala Asn Pro Pro Ala Pro Leu Asp Leu Leu Asp Glu Gly
    105                 110                 115 ggc tct tac cgt ttc gag cgc ttc gcc gac tac ctg gac gcg ttg cgg        438
Gly Ser Tyr Arg Phe Glu Arg Phe Ala Asp Tyr Leu Asp Ala Leu Arg
120                 125                 130                 135 gcc acg ccg gcg gcc gtc aac gcc gcc tgt atg gtg ggc cat tca acg        486
Ala Thr Pro Ala Ala Val Asn Ala Ala Cys Met Val Gly His Ser Thr
                140                 145                 150 ctg cgc gcc gcg gtc atg ccg gac ttg cag cgc gcc gcc acc gac gag        534
Leu Arg Ala Ala Val Met Pro Asp Leu Gln Arg Ala Ala Thr Asp Glu
            155                 160                 165 gaa atc gcg gcc atg cgg gac ctg gcc gag gaa gcc atg gcc agc ggc        582
Glu Ile Ala Ala Met Arg Asp Leu Ala Glu Glu Ala Met Ala Ser Gly
        170                 175                 180 gcc atc ggc att tcg acc ggc gcc ttc tac ccg ccc gcc gcc cgc gcc        630
Ala Ile Gly Ile Ser Thr Gly Ala Phe Tyr Pro Pro Ala Ala Arg Ala
    185                 190                 195
```

-continued

```
acc acc gaa gag atc atc gag gtg tgc cgg ccg ctg agc gcg cat ggc      678
Thr Thr Glu Glu Ile Ile Glu Val Cys Arg Pro Leu Ser Ala His Gly
200             205                 210                 215 ggc atc tac gcc acc cac atg cgc gac gaa ggc gag cac atc gtg gcc      726
Gly Ile Tyr Ala Thr His Met Arg Asp Glu Gly Glu His Ile Val Ala
                220                 225                 230 gcg ctg gag gaa acc ttc cgc atc ggc cgc gag ctg gac gtg ccg gtg      774
Ala Leu Glu Glu Thr Phe Arg Ile Gly Arg Glu Leu Asp Val Pro Val
            235                 240                 245 gtg atc tcg cac cac aag gtc atg ggc cag ccc aat ttc ggc cgc tcg      822
Val Ile Ser His His Lys Val Met Gly Gln Pro Asn Phe Gly Arg Ser
        250                 255                 260 cgc gag acg ctg ccg ctg atc gag gcc gcc atg gcg cgc cag gac gtc      870
Arg Glu Thr Leu Pro Leu Ile Glu Ala Ala Met Ala Arg Gln Asp Val
265                 270                 275 tcg ctg gac gcg tat ccc tac gtg gcc ggc tcc acc atg ctc aag cag      918
Ser Leu Asp Ala Tyr Pro Tyr Val Ala Gly Ser Thr Met Leu Lys Gln
280                 285                 290                 295 gac cgc gtg ctg ctg gcc gga cgc acc atc atc acc tgg tgc aag ccc      966
Asp Arg Val Leu Leu Ala Gly Arg Thr Ile Ile Thr Trp Cys Lys Pro
                300                 305                 310 ttc ccc gaa ctg agc ggg cgc gac ctg gat gaa gtc gcg gcc gag cgc     1014
Phe Pro Glu Leu Ser Gly Arg Asp Leu Asp Glu Val Ala Ala Glu Arg
            315                 320                 325 ggc aaa tcc aag tac gac gtg gtg ccc gag ctg cag ccg gcc ggc gcc     1062
Gly Lys Ser Lys Tyr Asp Val Val Pro Glu Leu Gln Pro Ala Gly Ala
        330                 335                 340 atc tac ttc atg atg gac gaa ccc gac gtg cag cgc atc ctg gcg ttc     1110
Ile Tyr Phe Met Met Asp Glu Pro Asp Val Gln Arg Ile Leu Ala Phe
345                 350                 355 ggc ccg acc atg atc ggc tcc gac ggc ctg ccg cac gac gag cgc ccg     1158
Gly Pro Thr Met Ile Gly Ser Asp Gly Leu Pro His Asp Glu Arg Pro
360                 365                 370                 375 cat ccg cgc ctg tgg ggc acc ttc ccg cgg gtg ctg ggg cac tat gcg     1206
His Pro Arg Leu Trp Gly Thr Phe Pro Arg Val Leu Gly His Tyr Ala
                380                 385                 390 cgc gac ctg ggc ctg ttc ccg ctg gag acg gcg gta tgg aag atg acc     1254
Arg Asp Leu Gly Leu Phe Pro Leu Glu Thr Ala Val Trp Lys Met Thr
            395                 400                 405 ggc ctg acc gcc gcg cgc ttc ggc ctg gcc ggg cgc ggg cag ctg cag     1302
Gly Leu Thr Ala Ala Arg Phe Gly Leu Ala Gly Arg Gly Gln Leu Gln
        410                 415                 420 gcc ggg tac ttc gcc gac ctg gtg gtg ttc gac ccg gcc acg gtg gcc     1350
Ala Gly Tyr Phe Ala Asp Leu Val Val Phe Asp Pro Ala Thr Val Ala
425                 430                 435 gat acc gcc acc ttc gaa cac cct acc gag cgc gcc gcc ggc atc cat     1398
Asp Thr Ala Thr Phe Glu His Pro Thr Glu Arg Ala Ala Gly Ile His
440                 445                 450                 455 tcc gtg tac gtc aac ggc gcg ccg gtc tgg caa gag cag gcg ttc acc     1446
Ser Val Tyr Val Asn Gly Ala Pro Val Trp Gln Glu Gln Ala Phe Thr
                460                 465                 470 ggc cag cat gcc ggc cgc gtg ctc gca cgc acg gcc gcc tgagcccggc      1495
Gly Gln His Ala Gly Arg Val Leu Ala Arg Thr Ala Ala
            475                 480 gccagcccctt acaatccggc gtgaacgggg cggcgtgccg ccccctccca accctggacg  1555
caaaccgcta catggcccct ccctccgctc gcaatacggc cccaccgat atcgtgggca    1615 aggaagtgat gggcgcgcgc ctgcgcgccg agcgcaaggc ccggaaaatg accctgcaag  1675
acctgtcgca ggccagcggc atcgcggtct cgaccctgtc caaggccgag ctgggccaga  1735
```
tcgccctgag ctacgagaag ctt                                            1758

<210> SEQ ID NO 2
<211> LENGTH: 484
<212> TYPE: PRT
<213> ORGANISM: Alcaligenes xylosoxydans subsp. xylosoxydans

<400> SEQUENCE: 2

```
Met Ser Gln Ser Asp Ser Gln Pro Phe Asp Leu Leu Ala Gly Gly
1               5                   10                  15

Thr Leu Ile Asp Gly Ser Asn Thr Pro Gly Arg Arg Ala Asp Leu Gly
            20                  25                  30

Val Arg Gly Asp Arg Ile Ala Ala Ile Gly Asp Leu Ser Asp Ala Ala
        35                  40                  45

Ala His Thr Arg Val Asp Val Ser Gly Leu Val Val Ala Pro Gly Phe
    50                  55                  60

Ile Asp Ser His Thr His Asp Asp Asn Tyr Leu Leu Arg Arg Arg Asp
65                  70                  75                  80

Met Thr Pro Lys Ile Ser Gln Gly Val Thr Thr Val Val Thr Gly Asn
                85                  90                  95

Cys Gly Ile Ser Leu Ala Pro Leu Ala His Ala Asn Pro Pro Ala Pro
            100                 105                 110

Leu Asp Leu Leu Asp Glu Gly Gly Ser Tyr Arg Phe Glu Arg Phe Ala
        115                 120                 125

Asp Tyr Leu Asp Ala Leu Arg Ala Thr Pro Ala Ala Val Asn Ala Ala
    130                 135                 140

Cys Met Val Gly His Ser Thr Leu Arg Ala Ala Val Met Pro Asp Leu
145                 150                 155                 160

Gln Arg Ala Ala Thr Asp Glu Glu Ile Ala Ala Met Arg Asp Leu Ala
                165                 170                 175

Glu Glu Ala Met Ala Ser Gly Ala Ile Gly Ile Ser Thr Gly Ala Phe
            180                 185                 190

Tyr Pro Pro Ala Ala Arg Ala Thr Thr Glu Glu Ile Ile Glu Val Cys
        195                 200                 205

Arg Pro Leu Ser Ala His Gly Gly Ile Tyr Ala Thr His Met Arg Asp
    210                 215                 220

Glu Gly Glu His Ile Val Ala Ala Leu Glu Glu Thr Phe Arg Ile Gly
225                 230                 235                 240

Arg Glu Leu Asp Val Pro Val Val Ile Ser His His Lys Val Met Gly
                245                 250                 255

Gln Pro Asn Phe Gly Arg Ser Arg Glu Thr Leu Pro Leu Ile Glu Ala
            260                 265                 270

Ala Met Ala Arg Gln Asp Val Ser Leu Asp Ala Tyr Pro Tyr Val Ala
        275                 280                 285

Gly Ser Thr Met Leu Lys Gln Asp Arg Val Leu Leu Ala Gly Arg Thr
    290                 295                 300

Ile Ile Thr Trp Cys Lys Pro Phe Pro Glu Leu Ser Gly Arg Asp Leu
305                 310                 315                 320

Asp Glu Val Ala Ala Glu Arg Gly Lys Ser Lys Tyr Asp Val Val Pro
                325                 330                 335

Glu Leu Gln Pro Ala Gly Ala Ile Tyr Phe Met Met Asp Glu Pro Asp
            340                 345                 350

Val Gln Arg Ile Leu Ala Phe Gly Pro Thr Met Ile Gly Ser Asp Gly
        355                 360                 365
```

```
-continued

Leu Pro His Asp Glu Arg Pro His Pro Arg Leu Trp Gly Thr Phe Pro
    370                 375                 380

Arg Val Leu Gly His Tyr Ala Arg Asp Leu Gly Leu Phe Pro Leu Glu
385                 390                 395                 400

Thr Ala Val Trp Lys Met Thr Gly Leu Thr Ala Ala Arg Phe Gly Leu
                405                 410                 415

Ala Gly Arg Gly Gln Leu Gln Ala Gly Tyr Phe Ala Asp Leu Val Val
                420                 425                 430

Phe Asp Pro Ala Thr Val Ala Asp Thr Ala Thr Phe Glu His Pro Thr
            435                 440                 445

Glu Arg Ala Ala Gly Ile His Ser Val Tyr Val Asn Gly Ala Pro Val
    450                 455                 460

Trp Gln Glu Gln Ala Phe Thr Gly Gln His Ala Gly Arg Val Leu Ala
465                 470                 475                 480

Arg Thr Ala Ala

<210> SEQ ID NO 3
<211> LENGTH: 6
<212> TYPE: DNA
<213> ORGANISM: Artificial
<220> FEATURE:
<223> OTHER INFORMATION: Nucleotide sequence in ribosome binding site
      for improving translation efficiency.

<400> SEQUENCE: 3 gaagga                                                                 6
```